United States Patent [19]
Mettler

[11] Patent Number: 6,060,045
[45] Date of Patent: May 9, 2000

[54] VITAMINIZED AIR FRESHENER AND ROOM DEODORIZER PAD

[76] Inventor: Leo Mettler, 8352 W. Granite Dr., Granite Bay, Calif. 95746

[21] Appl. No.: 09/270,340

[22] Filed: Mar. 16, 1999

Related U.S. Application Data

[63] Continuation-in-part of application No. 09/034,215, Feb. 28, 1998, Pat. No. 5,891,427, which is a continuation-in-part of application No. 08/629,407, Apr. 8, 1996, abandoned.

[51] Int. Cl.⁷ .................. A61L 9/00; A61L 9/01; A61L 9/14; B01D 53/34; A61K 7/32
[52] U.S. Cl. .................. 424/76.21; 424/65; 424/76.1; 424/76.2; 424/76.6; 514/904; 514/957; 514/959
[58] Field of Search .................. 424/76.21, 65, 424/76.1, 76.2, 76.6; 514/906, 957, 959

[56] References Cited

U.S. PATENT DOCUMENTS

| | | | |
|---|---|---|---|
| 4,851,212 | 7/1989 | Winston et al. | 424/45 |
| 4,946,870 | 8/1990 | Partain et al. | 514/777 |

*Primary Examiner*—Jeffrey Stucker
*Assistant Examiner*—Brett Nelson
*Attorney, Agent, or Firm*—Mark C. Jacobs, Esq.

[57] ABSTRACT

Wicks or pads for use in vitaminized air fresheners and room deodorizer devices are disclosed, which permit devices occupants to directly receive and enjoy the benefits of vitamins with little or no effort intra-nasally as they breath the released volatile compositions. A method for the continuous release of a vitamin containing composition for the delivery of discrete droplets intra nasally absorbed vitamins such as, but not limited to A, C, and D is also disclosed.

13 Claims, No Drawings

VITAMINIZED AIR FRESHENER AND ROOM DEODORIZER PAD

RELATION TO OTHER APPLICATIONS

This application is a continuation-in-part of application 09/034,215 filed Feb. 28, 1998, now U.S. Pat. No. 5,891,427, which is a continuation-in-part of application 08/629,407 filed Apr. 8, 1996, now abandoned.

FIELD OF THE INVENTION

This application pertains to room deodorizers and air fresheners disposed within a fibrous pad which serves as a carrier for the delivery of vitamins to the occupants of a room in a non-film forming manner.

BACKGROUND OF THE INVENTION

Cooking foods such as cabbage, the presence of cats and dogs, cigar smoke, burnt toast among other things are all sources of offending olfactory sensations. To alleviate these odors room deodorizers and air fresheners were invented. The first ones were liquids that were delivered through wicking action from a reservoir, Airwick™ was an early product of such category.

The next product to come along which still exist in the marketplace are the propellant-based air fresheners and room deodorizers. Previously they used fluorocarbons as the propellent, but more recently isobutane has become the propellant of choice.

The difference between a room deodorizer and an air freshener is that an air freshener only marks the odor that is present, while a deodorant "eats" or destroys the odor present by a believed chemical reaction.

The benefits of vitamins and minerals in tableted form as food supplements are quite well documented. Indeed many people in the U.S.A. and elsewhere take vitamin C tablets to ward off colds. Others take vitamin E to retard the signs of aging and to hasten the healing of cuts and wounds.

It is also well known that the delivery of tabletized and pelletized vitamins to the body is slow due to the need for these to be chewed up and digested prior to the delivery of their precious benefits to the human body.

Vitamin therapy is one of the fastest growing areas of health maintenance. Today antioxidants is a big buzz word and vitamin C is indeed such a compound. Thus, it is seen to be beneficial to take vitamin C, as was first popularized by Dr. Linus Pauling.

There are many factors that determine the amount of benefit one can device from the ingestion of vitamin C. Each individual reacts differently. The dissolving rate in the body and the amount of the vitamin actually absorbed by every person is different when considered alone. Add to the equation the presence of various types and quantities of food in the stomach and the intestine, and again the absorbency rate can be and is affected. Also some people suffer diarrhea or stomach irritation from the vitamins in pill format.

Recent research has shown that intra nasal delivery systems may be superior to oral delivery of vitamins such as A, C and E. The cell systems of the nasal cavity have been found to absorb certain vitamins rapidly and efficiently, thereby avoiding degradation of the vitamins by stomach acid, and the inhibition of delivery of benefits, due to the presence of food in stomach or intestine.

Vitamins and other medicaments that are delivered indirectly such as by being forced to exude from a film forming material such as the aminopolysaccharides and their derivatives as disclosed in claimed in Partain et al, U.S. Pat. No. 4,946,870 while perhaps delivering the intended medicament, do so ever more slowly than can be accomplished using the procedure of this invention. In the Partain procedure the medicament is introduced into the body topically indirectly, in that the medicine must be laid down in the film carrier and then absorbed. Whereas in this invention, the discrete droplets of the aerosol spray, or the droplets from the dissemination from a pad from the air blowing over the pad, produce discrete tiny droplets that are easily ingested during breathing. Such an introduction is preferable. Granted that Partain can use an aerosol for delivery, but the object is to form a film first and then to ingest from the film, whereas in the Mettler procedure, the ingestion is direct without any dwell time within a film carrier.

Of course, the intent of Partain is totally different from the intent of Mettler. Partain seeks to medicate an individual with a medicine directed to that person's attention. But for Mettler who has been active in the room deodorizer business for many years, witness his several United States patents in that field of endeavor, the intent is to provide an improved room deodorizer than benefits anyone and everyone who enters the room, by permitting those people to gain the benefits of propellant delivered vitamins present in the mist or discrete droplets of the air of a nicely smelling room. Additionally, any of the compositions of this invention as released from the wick or pad that might impact furniture, would not leave any type of film or stain thereon.

At least one cold remedy; namely, Primatene Mist which contains bronchial dilator ingredients delivers ascorbic acid along with its other ingredients in an attempt to aid the respiration of an ill person. But this device is not one for general delivery into the environment, i.e., a whole room.

Unfortunately most people do not want to carry around personal inhalers to shove up their nostrils to receive medicated vitamin C especially when there is no difficulty in breathing. Also children don't know how to use these inhalers.

Thus there was found to be a need for a way to nasally deliver vitamins to the nasal passages of the general populous without the need for an inhaler.

It is an object therefore of this invention to provide a breathable composition that contains vitamin C and/or vitamin E.

It is an additional object to provide a vitaminized composition that can be used to mask and/or deodorize ambient air and which is readily deliverable.

It is a further object to provide a pad in the shape of wick or in the shape of a disk, impregnated with a vitaminized composition for direct nasal delivery of vitamins C and E.

It is yet another object to provide a process for the regular and continuous delivery of vitamins C and/or E to the nose without the need for a personal inhaler to fit up the nostril.

It is a still further object to provide a vitaminized room deodorizer pad that can bring vitamins to the occupants of the room which has a pleasing aroma.

It is a yet further object to provide a vitaminized air freshener that can bring vitamins to the occupants of a room from a discrete relatively small quiet apparatus.

It is one further object to provide a method for the continuous periodic delivery of vitamins to the occupants of a room.

These and other objects of the invention will in part be obvious and will in part appear hereinafter.

The invention accordingly comprises the device possessing the features properties and the relation of components which are exemplified in the following detailed disclosure and the scope of the application of which will be indicated in the appended claims.

For a fuller understanding of the nature and objects of the invention reference should be made to the following detailed description, taken in conjunction with the accompanying drawings, if present.

SUMMARY OF THE INVENTION

A vitaminized air freshener and a vitaminized room deodorizer are disclosed which permit occupants to receive and enjoy the benefits of vitamins with little or no effort. The air freshener and room deodorizer are impregnated onto a fibrous pad configured as a wick or as a disk such that release can transpire into the environment of a room over an extended period of time.

DESCRIPTION OF THE PREFERRED EMBODIMENT

The compositions of this application are for both air fresheners which mask odors and for room deodorizers which actually destroy odors, both of which can deliver solubilized vitamins to occupants of a room.

Among the solublizable vitamins mention may be made of vitamin A, (beta carotene), vitamin C and vitamin E. These and other soluble vitamins can be employed solely or in combinations.

As to the propellants suitable for my compositions, mention may be made of the various fluorocarbons which now have been banned in some countries, isobutane, nitrogen and other organic propellants available in the marketplace.

Any fragrance oil such as wood, such as pine scent, orange, lemon or lime, other fruits such as peach, and flower derived fragrances may be employed. Flower derived fragrances include those available in the marketplace from such vendors as Belle Aire Fragrances of Highland Park Illinois among others. These flower derived fragrances include but are not limited to the ode de chrysanthemum, rose, jasmine, lavender, gardenia and others. Various potpourri that are available as fragrance oils may also be employed.

Fragrance oils are employed within the range of 0.75% to 2.5% of the weight of the composition. Preferably about 1% of fragrance is employed. Fragrance bases are available from many sources in the marketplace.

While it is believed that any solubilizable vitamin may be employed, particularly good results have been obtained with vitamins A, C and E between about 1 and about 12% by weight Among the alcohols that can be utilized in these compositions, mention may be made of ethanol, propanol and isopropanol. Alcohols are employed within the range of 92 to 96 percent by weight of the total composition to solubilize the vitamin(s) and the fragrance oil.

As noted earlier room deodorants include a glycol such as, but not limited to, dipropylene glycol. Other suitable glycols include diethylene glycol, and triethylene glycol. The level of glycol within the formulation would range from five percent (5%) to about twenty percent (20%) by weight. Since the alcohol is the conventional solubilizing agent employed, the amount of alcohol is reduced by the amount of glycol added to the total composition.

GENERALIZED PREPARATION PROCEDURE

To a finite amount of alcohol is added any solid or powdered vitamin. The mixture is heated below boiling to dissolve the vitamin such as vitamin C using mild agitation during the heating process. First, the mixture of alcohol and dissolved vitamin is permitted to cool to room temperature.

Then, the fragrance oil, in a second step is added as is any glycol should the end product be a deodorizer under mild heat with agitation. After thorough blending the mixture is cooled to ambient temperature and is ready for filling in the spray can or other delivery device along with the propellant.

The filling and use of propellant based sprays is at this point in time deemed conventional. Thus there need be no further discussion of how these mixtures are utilized with propellants to become spray compositions.

The following specific examples are typical of the air freshener and room deodorizer composition mixtures which contain one or more soluble vitamins that can be prepared according to this invention. These examples are exemplifications only and are not to be considered as limiting.

EXAMPLE I

| Ingredients | Wt. % of Composition |
|---|---|
| Fragrance Oil | 1% |
| Vitamin(s) | 4% |
| Alcohol | 95% |
| | 100% |

EXAMPLE II

| Ingredients | Wt. % | Weight |
|---|---|---|
| Fragrance Oil Jasmine | 2% | .030 oz. |
| Ascorbic Acid | 1% | .015 oz. |
| Vitamin E Oil | 2% | .030 oz. |
| Alcohol | 95% | 1.125 |
| | 100% | 1.500 oz. |

To this 1.5 ounces of formulation is added 5.6 ounces of a propellant known in the trade as A70 to achieve a total net content of 7.1 ounces.

EXAMPLE III

| Ingredients | Wt. % | Ounces |
|---|---|---|
| Fragrance Oil - Summer Flowers | 1% | .015 oz. |
| Ascorbic Acid | 2% | .020 oz. |
| Vitamin E Oil | 2% | .030 oz. |
| Dipropylene Glycol | 10 | .150 oz. |
| Propyl Alcohol | 85 | 1.275 oz. |
| | 100% | 1.500 oz. |

EXAMPLE IV

| Fragrance Oil - Pine | 1% |
|---|---|
| Beta Carotene | 2% |
| Isopropyl Alcohol | 97% |
| | 100% |

EXAMPLE V

| Fragrance Oil - Lemon | 1% |
|---|---|
| Ascorbic Acid | 2% |
| Diethylene Glycol | 22% |
| Ethanol | 73% |
| | 100% |

EXAMPLE VI

| Fragrance Oil - Peach | 1% |
|---|---|
| Vitamin E | 5% |
| Isopropyl Alcohol | 94% |
| | 100% |

EXAMPLE VII

| Fragrance Oil - Lime | 2% |
|---|---|
| Ascorbic Acid | 6% |
| Dipropylene Glycol | 20% |
| Propyl Alcohol | 72% |
| | 100% |

It is also to be understood that a room deodorizer formulation can be easily modified to create a vitaminized medicated decongestant for delivery to the occupant(s) of the room by the addition of one or more of such ingredients as thymol, menthol, camphor and eucalyptus oil.

EXAMPLE IX

A typical formulation for a product would be:

| Thymol | 0–2% |
|---|---|
| Menthol | 0–6% |
| Camphor | 0–6% |
| Eucalyptus oil | 0–2% |
| Vitamin E | 0–5% |
| Ascorbic Acid | 0–5% |
| Dipropylene Glycol | 10–25% |
| Ethanol | Balance |
| | 100% |

EXAMPLE X

A more specific decongestant formulation would be:

| Thymol | 1.20% |
|---|---|
| Menthol | 6.0% |
| Camphor | 6.0% |
| Eucalyptus Oil | 1.80% |
| Dipropylene Glycol | 22.00% |
| Ethanol Vanzol | 59.00% |
| Ascorbic Acid | 2.00% |
| Vitamin E Oil | 2.00% |
| Total | 100% |

One mode of delivery of these vitaminized mixtures to the nasal passage is by an automatic spray delivery system. Such a pressurized dispenser forms the subject matter of U.S. Pat. No. 3,974,941 issued Aug. 17, 1976 to Leo Mettler. The text and claims of this Mettler patent is hereby incorporated by reference into this application. When so packaged the mixtures are referred to as spray compositions.

This patented battery operated dispenser includes an electronic timer circuit such that it can deliver a timed dose of vitamin C, or E, or A among others alone or in combination into the atmosphere of the room where the dispenser is situated. Thus, at any time interval between 5 seconds and 30 minutes as may be user determined, a spray of the vitaminized compositions of this invention can be released into the environment. The ability to control the frequency of emission of a constant quantity of the composition permits the user to compensate for the size of the room, the airflow, and the number of occupants as may be desired.

The dose of the vitamin(s) absorbed by the body intranasally from the mist in the room depends upon (1) the vitamin concentration in the formulation, and (2) the volume of actual solution (versus propellant) that is delivered each time this applicator (or any application) is actuated. Studies have shown that the body intake and utilization is significantly higher nasally than orally due to the lack of interference by stomach acid and the time necessary to get into the system.

It is seen that an air freshener and a room deodorizer are similar to a room spray decongestant formulation, if one considers such compositions to be the carrier for the vitamin being delivered. The fragrant mist can be a pleasurable way to provide the user with a daily intake of supplement vitamins. If the carrier composition is a decongestant, then the added benefits of the thymol, and eucalyptus oil in addition to the vitamin benefits can be obtained.

Such an automated delivery system permits the parties present to work or play unimpeded in a vitaminized environment without the need for special inhaler equipment the latter of which can be extremely motion limiting.

While another mode of delivery of the vitaminized compositions is by a finger actuated spray cans, which is readily available in the marketplace from many companies, a more preferred mode of delivery is to load these vitaminized mixtures onto compressed fiber pads through which air can be forced via a fan blowing air on the pad. Such an apparatus is disclosed and claimed in the Mettler U.S. Pat. No. 4,301,095 issued Nov. 17, 1981.

In this reference there is described a motorized apparatus which includes a fan whose purpose is to spread the contents found impregnated into a fibrous disk into the ambient environment. Such wicks are also known as a conditioning element in the trade. Such elements as would be used in the Mettler patent are readily understandable and are shown in FIG. 7 of the Mettler U.S. Pat. No. 4,301,095. The text of column four, lines 55–63 and FIG. 7 of the Mettler U.S. Pat. No. 4,301,095 are incorporated herein by reference.

Thus briefly, the conditioning element includes a generally fibrous disk of felt, paper, sponge, artificial sponge or other absorbent materials known to science from which a volatile fluid may be delivered by the impingement of an air stream in the conditioning element.

For use in the Mettler apparatus each conditioning element should be annular and range from 1.5 to about 3 inches in diameter and be from about 3/16 inch to 1/2 inch thick. The preferred conditioning element for a Mettler-type device is annular such that it can be mounted on to a retention collar to be disposed within the central opening of the annulus device.

In order to load the conditioning element with the liquid composition, the element is placed into an individual plastic carrier tray bottom, injected with the solution, and the plastic carrier bottom is then sealed with a closure to segregate the element absorbed from the environment.

While the annular disk is the preferred configuration for the Mettler appliance of U.S. Pat. No. 4,301,095, other shapes such as a tampon, i.e., an elongated cylinder may also be employed. Cylindrical pads can be retained by a pair of spaced fingers, akin to a paper towel holder.

Other shapes of compressed fibrous pads are also within the scope of the invention, as the means for retention of the vitaminized composition of this invention by having air flow over the pads to release its volatile composition contents.

For delivery to room occupants the basic mixtures must be modified for several reasons. In the format of a pad exposed to the environment an alcohol solution would evaporate quite quickly. Therefore, the alcohol content needs to be reduced and is in part replaced by additional fragrance oil and volatilization inhibitor.

Thus a typical formulation for pad delivery would be:

| Example XI | % | Wt/Pad |
| --- | --- | --- |
| Fragrance Oil | 60% | 4.80 gms |
| IGEPAL ® CA 630 | 32% | 2.56 gms |
| Ascorbic Acid | 0–4% | .16 aver. |
| Vitamin E | 0–4% | .16 aver. |
| Alcohol | 4% | .32 |
|  | 100% | 8.00 gms |

IGEPAL® is a trademark of GAF Corp for a series of biodegradable non-ionic surfactants used as detergents, dispersants, emulsifiers and wetting agents and is used here to prevent volatilization.

It is to be noted that the IGEPAL® can be replaced by an equal amount of Hercolyn D which a hydrogenated methyl ester of rosin. It is used as a plasticizer.

The ingredients are mixed and heated together until the vitamin(s) solubilize.

The mix is allowed to cool to room temperature and applied to the pads by conventional machinery. The pads are packaged to retain the contents until ready for placement in a machine such as the one claimed in U.S. Pat. No. 4,301,095 issued to Leo Mettler.

It is to be further noted that the amount of alcohol in the mixture for pads can vary between 3 and 10%.

It is seen that I have provided mixtures that can be readily absorbed into the body for delivery of the vitamins therein intra-nasally through their delivery in any of an air freshener, room deodorizer or a decongestant-inhaler, as a spray into the room, or by forced air delivery into the room.

Thus it is seen that the timed spray delivery of a vitaminized decongestant during sleep periods, will both relieve symptoms of colds, hay fever and sinusitis, while eliminating the use of a water vaporizers which tend to increase the level of dampness of a room, which could cause mildew, a new irritant to the occupant.

Previously it has been mentioned that the compositions of this invention are intended for delivery of vitamins to the occupants of a room directly intra nasally. These compositions can be introduced in the form of an aerosol which will create discrete droplets in a mist of a room deodorizer as is conventionally known and the compositions can be introduced to the occupants by having the compositions impregnated onto a compressed fiber pad, over which flows compressed air or another inert gas to introduce the composition into the room and thus directly to the nasal passages of the occupants of the room. Such a device is disclosed and claimed in my U.S. Pat. No. 3,974,941 entitled Automated Aerosol Mist Dispenser.

In order to further demonstrate that the compositions disclosed and claimed herein, be they introduced from a spray container or mist dispenser do not form a film on room furnishings, the following tests were carried out:

1. A 1.5 ounce net sample of the formulation of Example I of the pending application was put into an aerosol can along with 5.6 ounces of a propellant, using conventional technology and I sprayed an amount that comes out with two finger presses of the atomizer valve, at a distance of about 2 feet onto the black surface of a home video recorder and allowed the spray to dry. No visual appearance of droplets and no residual was seen on the black surface. A clean white facial tissue was wiped over the area that received the spray, and then observed. No film or other deposit was found to be visible on the facial tissue.

2. The test described above was repeated using the formulation of Example I of the pending patent application 1.5 ounces and 5.6 ounces of the propellant onto a white household flat paper surface. Again no visible film or deposit was visible to the naked eye on either the white surface or the white facial tissue.

3. Using an automatic periodic dispenser to release the product at 15 minute intervals, with the spray nozzle of the dispenser located approximately 15 inches above the table top and released a spray length of approximately 3 feet long horizontal to the table surface for a period of 24 hours for a total of 96 spray releases. No residual of any type was found on the furniture surfaces after visual inspection.

Since certain changes may be made in the above described compositions without departing from the scope of the invention herein involved, it is intended that all matter contained in the above description shall be interpreted as illustrative and not in a limiting sense.

I claim:

1. A compressed fiber pad impregnated with a composition which pad is adapted for impact by an inert gas for the aerosol dispersal of droplets of a by weight mixture consisting essentially of
    (a) fragrance oil—about 0.75% to about 2.5%
    (b) at least one soluble vitamin—about 1% to about 12%;
    (c) alcohol—the balance in weight percent to equal 100%, which pad is adapted to release the mixture into the environment upon the impact of forced air.

2. The impregnated compressed fiber pad of claim 1 wherein the mixture consists essentially of:
(a) a fragrance—about 2%
(b) a mixture of vitamin E and ascorbic acid combined at about 3%,
(c) alcohol—about 95%.

3. The impregnated compressed fiber pad of claim 2 further including:
Thymol 0–2%
Menthol 0–6%
Camphor 0–6%
Eucalyptus Oil 0–2%
within the total weight of the mixture.

4. The impregnated compressed fiber pad of claim 1 wherein the mixture consists essentially of:
(a) a fragrance—about 2%
(b) ascorbic acid at about 3%,
(c) and alcohol—about 95%.

5. The impregnated compressed fiber pad of claim 4 further including a volatilization inhibitor.

6. The impregnated fiber pad of claim 1, wherein the pad is a disk of about 2.5 inches in diameter.

7. The impregnated pad of claim 1, wherein the pad's material is selected from the group consisting of felt, paper, sponge and artificial sponge.

8. The impregnated pad of claim 1 wherein between about 10% and 25% of the alcohol in the composition is replaced by a glycol.

9. The impregnated pad of claim 1, wherein the pad is shaped like a wick.

10. An impregnated pad for use in a room deodorizer device which device is adapted to force a gaseous fluid to impact the pad to release the contents into a room, wherein the pad is impregnated with a composition consisting essentially of:
(A) jasmine fragrance—about 2%
(B) a soluble vitamin mixture of vitamin E and ascorbic acid—about 3%
(C) about 95% alcohol by weight.

11. The impregnated pad of claim 10 wherein the pad is an annular disk.

12. A method of periodically introducing vitamins to the occupants of a room via aerosol dispersal, which comprises:
(a) periodically passing an inert gas over a compressed fiber pad, disposed in a housing having an exit opening, which pad is impregnated with a composition consisting essentially of a by weight mixture of:
(b) fragrance oil—about 0.75% to about 2.5%
(c) at least one soluble vitamin—about 1% to about 12%, and
(d) alcohol—the balance in weight percent to equal 100% to introduce a mist of the composition into the environment from time to time.

13. The method of claim 12 wherein the soluble vitamin is selected from the group consisting of vitamin C, vitamin E, and mixtures thereof.

* * * * *